United States Patent [19]

Lindquist

[11] Patent Number: 5,447,506
[45] Date of Patent: Sep. 5, 1995

[54] ABSORPTION BODY

[75] Inventor: Bengt Lindquist, Lerum, Sweden

[73] Assignee: Mölnlycke AB, Gothenburg, Sweden

[21] Appl. No.: 135,654

[22] PCT Filed: Dec. 6, 1989

[86] PCT No.: PCT/SE89/00713

§ 371 Date: Jun. 6, 1991

§ 102(e) Date: Jun. 6, 1991

[87] PCT Pub. No.: WO90/06096

PCT Pub. Date: Jun. 14, 1990

Related U.S. Application Data

[63] Continuation of Ser. No. 687,934, Jun. 6, 1991, abandoned.

[30] Foreign Application Priority Data

Dec. 6, 1988 [SE] Sweden ................. 8804402

[51] Int. Cl.6 .................. A61F 13/15; B32B 5/14
[52] U.S. Cl. ...................... 604/374; 604/379; 604/385.1; 428/170; 428/171
[58] Field of Search ............. 604/378, 383, 368, 358, 604/388.1, 904, 374; 428/176, 171; 602/41–47

[56] References Cited

U.S. PATENT DOCUMENTS

| 2,566,451 | 9/1951 | Julien | 604/380 |
|---|---|---|---|
| 2,964,039 | 12/1960 | Johnson, Jr. et al. | 604/378 |
| 2,973,760 | 3/1961 | Dudley | 604/378 |
| 3,430,630 | 3/1969 | Megison et al. | 604/380 |
| 3,545,441 | 12/1970 | Gravdahl et al. | |
| 3,621,847 | 11/1971 | Roberson | 604/368 |
| 3,860,002 | 1/1978 | Kolbach | 604/380 |
| 4,174,721 | 2/1978 | Smits et al. | 604/380 |
| 4,184,498 | 1/1986 | Franco | 604/379 |
| 4,333,463 | 6/1982 | Holtman | 607/378 |
| 4,624,666 | 1/1986 | De Russett et al. | 604/379 |
| 4,758,240 | 7/1988 | Glassman | 604/379 |
| 4,826,295 | 4/1989 | Chapas et al. | 604/379 |

FOREIGN PATENT DOCUMENTS

| 0169184 | 1/1986 | European Pat. Off. | |
| 1815541 | 12/1968 | Germany | 604/379 |
| 2127678 | 6/1971 | Germany | 604/379 |
| 0222264 | 9/1968 | Sweden | 604/358 |
| 349476 | 10/1972 | Sweden | |
| 0013278 | 11/1990 | WIPO | 604/379 |

Primary Examiner—Randall L. Green
Assistant Examiner—K. M. Reichle
Attorney, Agent, or Firm—Burns, Doane, Swecker & Mathis

[57] ABSTRACT

The present invention relates to an absorption body intended for an absorbent product, such as a sanitary towel or an incontinence guard, and comprising an absorbent material, preferably cellulose fluff, which increases in quantity continuously from the edge margins of the article in towards the center part thereof. According to the invention, the absorption body is compressed to an essentially flat shape and exhibits a degree of compression which increases continuously from the edge margins towards the center part of the body. The invention also relates to a method of producing an essentially flat absorption body, the density of which increases continuously from the edge margins in towards the center part thereof.

15 Claims, 3 Drawing Sheets

ABSORPTION BODY

This application is a continuation, of application Ser. No. 07/687,934, filed Jun. 6, 1991, now abandoned.

BACKGROUND OF THE INVENTION

The present invention relates to an absorbent body intended for an absorbent article, such as a sanitary napkin or an incontinence guard, and comprising an absorbent material, such as cellulose fluff, which continuously increases in quantity from at least the side edges of said article in towards the centre thereof.

The most serious problem associated with the manufacture of sanitary napkins is one of producing a napkin which will not leak in use. The most common type of leakage is leakage from the sides of the napkin. Such leakage may have several causes. It may, for instance, be because the menstrual fluid disperses so poorly throughout the absorption body that the regions peripheral of the point of contact of the liquid with said body becomes quickly saturated, causing further liquid to flow beyond the edge margins of the towel. Another and more general reason is that the towel becomes distorted and squashed between the thighs of the wearer, so as to greatly reduce the area of the liquid-receiving surface of the towel. This latter problem is particularly manifest in modern sanitary towels, which are often made very narrow, so that the towel can be worn comfortably and discretely.

The Swedish Patent Specification No. 349 476 describes a sanitary towel or corresponding article, the absorbent body of which comprises fibrous absorbent material which varies gradually in quantity per unit of volume in the longitudinal and transverse directions of the towel.

The majority of this absorbent material is located in that part of the towel with which the liquid is first intended to come into contact, and the quantity of absorbent material contained in the body per unit of volume gradually decreases in a direction away from this region. In manufacture, this known absorption body has a thickness which is approximately the same over the whole area of the body, but which has latent expansion forces which are released when the towel is in use, such as to cause the centre part of the towel to expand. As a result of this expansion, the known towel adopts an ellipsoidal shape, which is said to be particularly desirable and to render the towel more comfortable when worn.

A significant drawback with this known sanitary towel is that the towel is soft and moldable and can therefore be squashed or likewise deformed in use, mainly in the transverse direction thereof, with a greater risk of leakage occurring in consequence thereof. Another serious drawback is that the sanitary towel swells in use, primarily in the direction of its thickness, thereby becoming less discrete when worn. It is found that the persons who use sanitary towels place great importance on the requirement that the towel is so discrete as to be unnoticeable when worn beneath everyday clothing. A discrete sanitary towel generally implies a towel which is thin. A thin or discrete towel is also considered by the majority of users to be more comfortable and pleasant to wear than a sanitary towel which is thick and bulky.

OBJECT AND SUMMARY OF THE INVENTION

The present invention provides an absorption body which is of the afore-described kind and which is intended for use in sanitary towels or incontinence guards, and which avoids the problems encountered with the known absorption bodies. An inventive absorption body is mainly characterized in that the absorbent body is compressed to a substantially flat shape and exhibits degrees of compression which increase continuously from the side edges of the body towards the centre part thereof.

An inventive absorption body is produced preferably by forming from an absorbent material, preferably from cellulose fluff, a blank which presents a generally triangular cross-sectional shape in the transverse direction of the blank, and by compressing the blank over the whole of its surface area with a force such that the edge margins of the absorption body will at least partially spring back when the compression force is removed, while the centre part of the absorption body will retain substantially the degree of compression achieved when applying the compressive force.

Further features of an absorption body constructed in accordance with the invention are set forth in the following claims.

An inventive absorption body provides a number of advantages. The heavily compressed centre part of the absorption body imparts good shape stability thereto and effectively counteracts forces which tend to squash or likewise deform said body. Despite the relative rigidity of the absorption body and its resistance to squashing or like compression forces, the edges of the body are soft and yieldable. Consequently, a sanitary towel or corresponding article which comprises an absorption body produced in accordance with the invention can be worn very comfortably. Such a sanitary towel will also possess a combination of attributes which has previously been impossible to achieve, namely the attributes of being highly absorbent and very discrete when worn.

The high absorption ability of the towel is due to the fact that the absorption body contains a relatively large quantity of absorbent material, and that the absorption material is utilized particularly effectively, due to the liquid-dispersion properties imparted to said body by said compression. Since liquid is transported most rapidly in fine capillaries, the liquid absorbed will first disperse in the longitudinal direction of the absorption body, because the material has a density which is high in this direction, which means that the space between the individual absorption fibres or particles will be small. On the other hand, when the regions of highest density become saturated with liquid, liquid will also disperse in the transverse direction of the towel.

Since the density of the absorption body increases continuously in a direction from the edge margins of the body towards the centre thereof, the size of the liquid-transporting channels between the absorption fibres will decrease to a corresponding extent in this direction. This means that liquid which is deposited close to the edge of the absorption body will be positively drawn by suction in towards the centre of said body, since liquid transportation always takes place from coarser to finer capillaries. Consequently, the edge margins of the absorption body will always remain dry, provided that the absorption capacity of the centre part of the towel has not been exhausted. The risk of side leakage with a sanitary towel provided with an inventive absorption body is therefore minimal, even should the towel be displaced somewhat sideways in use.

The small thickness of the absorption body enables the sanitary towel to be worn very discretely, and is, of course, also advantageous from a packaging aspect.

Because the absorption body is thinnest at its centre region, the body forms a liquid-receiving basin-shaped trough. The raised edge parts therewith form liquid-damming walls which prevent liquid from flowing beyond the edge margins of the towel, before the liquid can be absorbed. This is particularly advantageous in the case of incontinence guards, which must be capable of collecting a relatively large quantity of liquid within a relatively short time period.

BRIEF DESCRIPTION OF THE DRAWINGS

The present invention will now be described in more detail with reference to a sanitary towel provided with an inventive absorption body, and also with reference to embodiments illustrated in the accompanying drawings.

DESCRIPTION

Figures 1, 2:
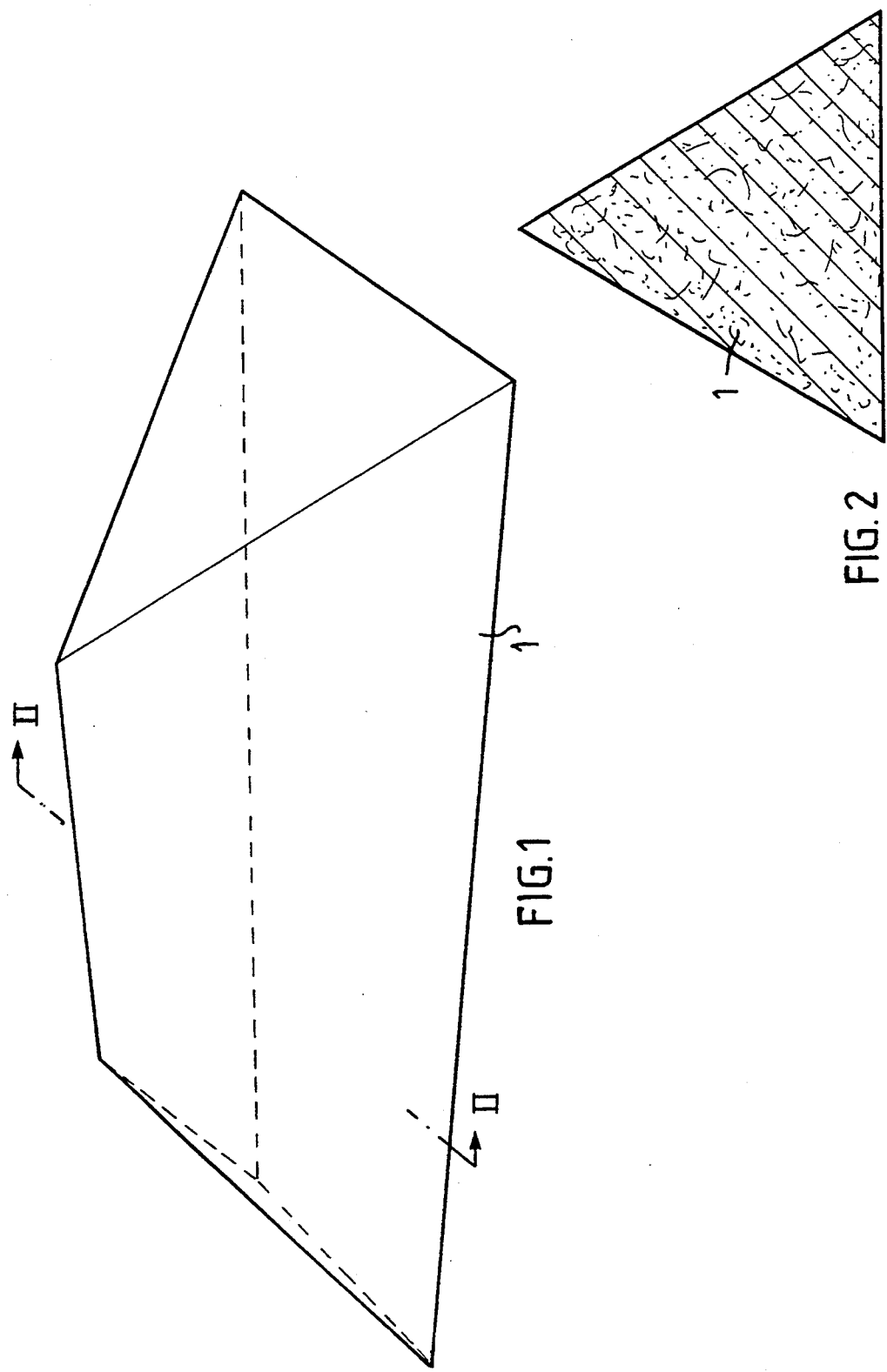
FIG. 1 illustrates an uncompressed blank from which an absorption body is formed.
FIG. 2 is a cross-sectional view of the blank shown in FIG. 1, taken on the line II—II in said figure.

The blank 1 shown in FIGS. 1 and 2 consists of cellulose fluff shaped so that the blank will have a generally triangular cross-sectional configuration. The major part of the absorption material of a blank 1 of this configuration will be concentrated essentially to the region around the longitudinal centre line of the blank. The absorption material from which the blank is formed gradually decreases in quantity from the centre line of said blank out towards the edge margins ending at the edge sides thereof. Compression of the blank 1 will result in an essentially flat absorption body. When the compression force applied is sufficiently high, the edge margins of the absorption body will spring back slightly when the force is removed, whereas the centre part of the body will retain the thickness imparted thereto by said compression.

Consequently, an absorption body produced in accordance with the invention will have its thinnest and most dense region around said centre line, where it contains a large quantity of absorption material, whereas the edge margins of the body are thicker and have lower density. The transition from the compressed centre part to the more voluminous edge margins of the body takes place gradually, without any visible boarder.

Figure 3:
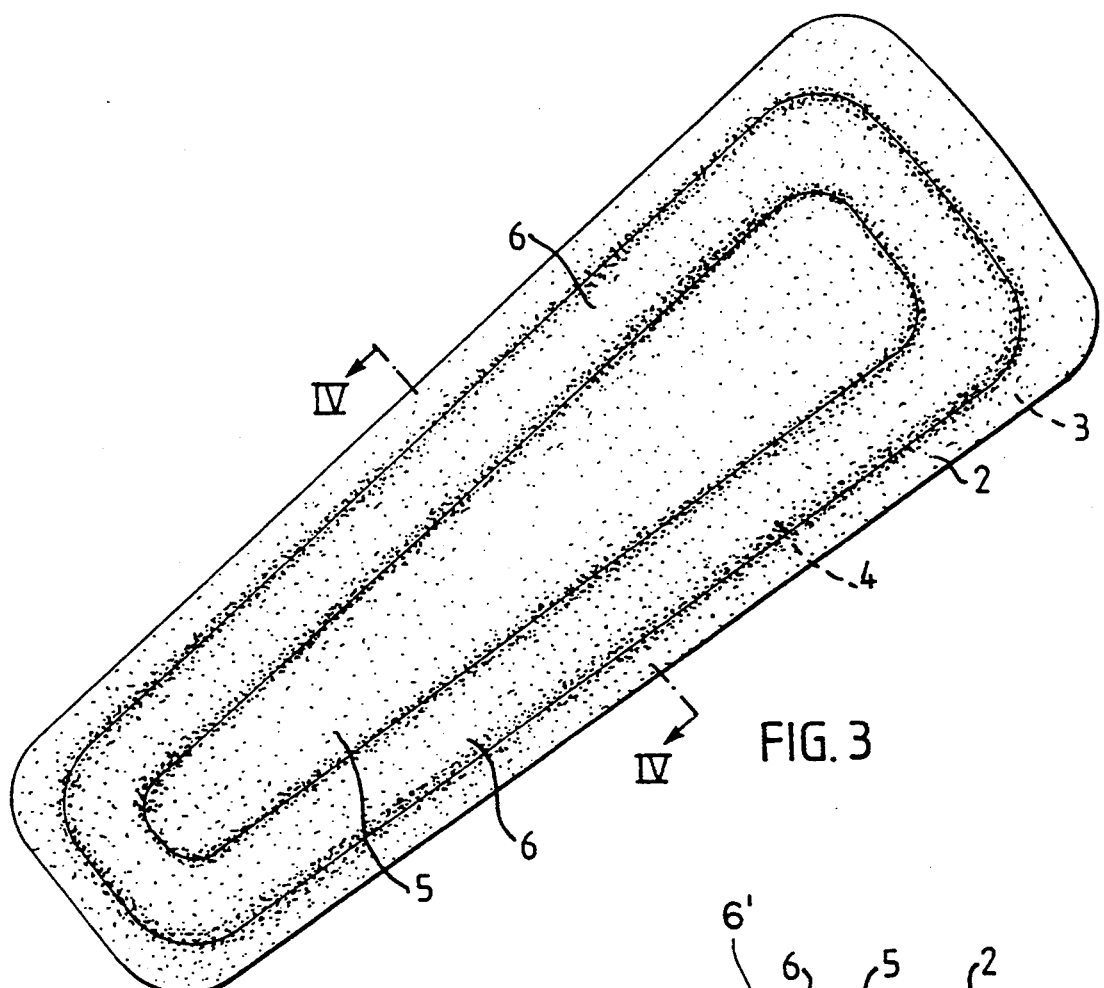
FIG. 3 is a view from above of a sanitary towel provided with a compressed absorption body.
Figure 4:
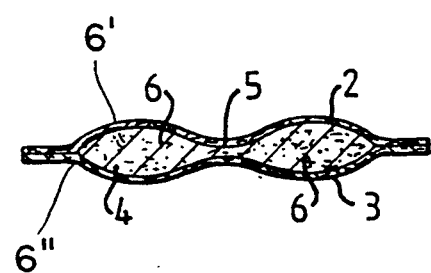
FIG. 4 is a sectional view taken on the line IV—IV in FIG. 3.

The sanitary towel illustrated in FIGS. 3 and 4 includes a liquid-permeable casing sheet 2, for instance fibre fabric or perforated plastics film, and a liquid-impermeable backing sheet 3, for instance plastic film or hydrophobic fabric. The sheets 2, 3 are mutually joined along their respective edge margins and enclose there between an absorption body 4.

In a preferred embodiment of the invention, as best seen in FIG. 4, the towel is thinnest at its center region 5, and gradually increases in thickness toward the edge margins 6 where the thickness reaches a maximum 6'. The towel then decreases in thickness from the maximum 6' to form the side edges 6" where the absorbent material ends. As previously mentioned, there is formed in this way a basin-like, liquid-receiving area 5 along the centre line of the towel, whereas the raised edge-margins 6 function as liquid-damming abutment surfaces against the wearer's body.

Figure 5:
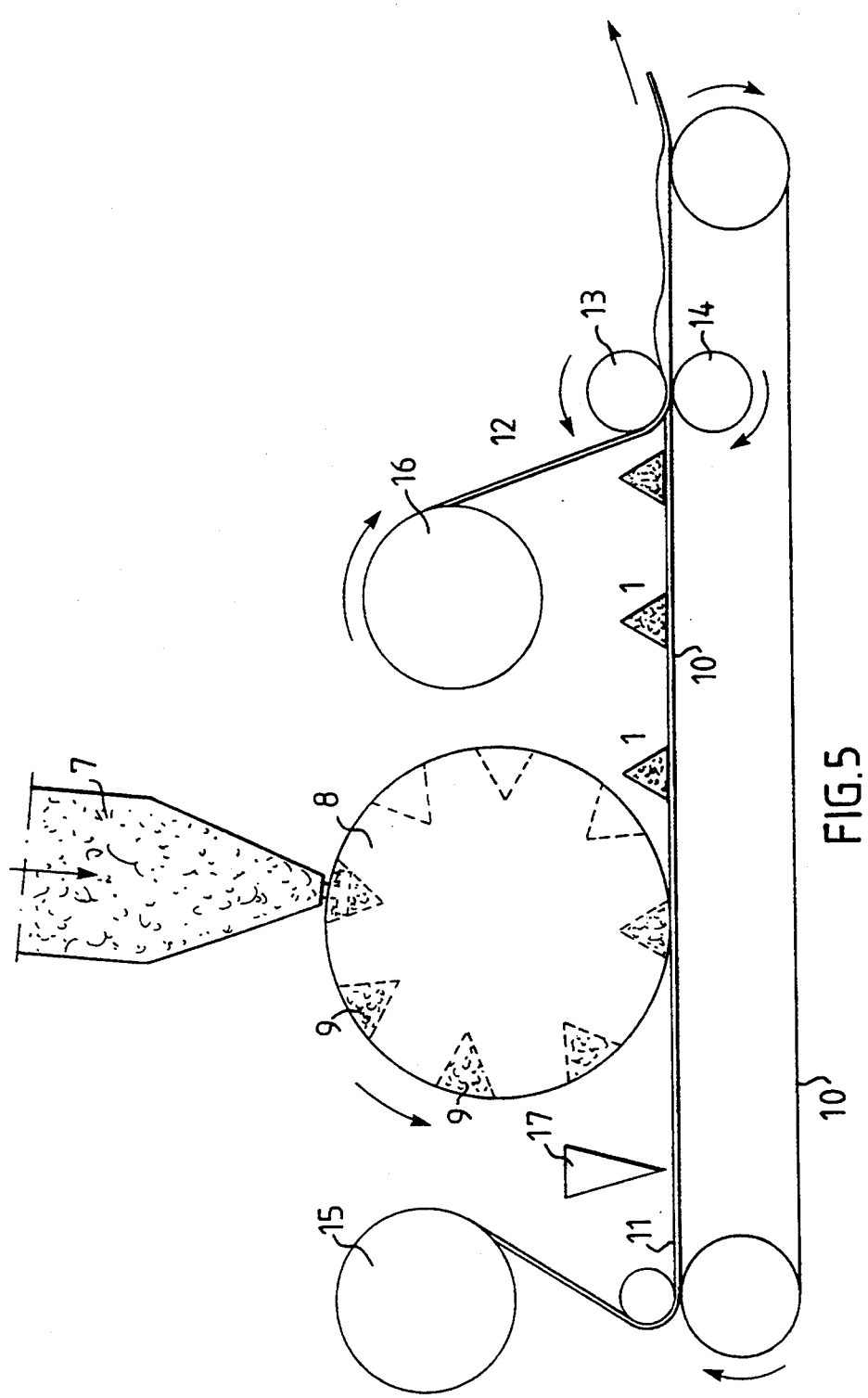
FIG. 5 illustrates schematically the manufacture of the sanitary towel illustrated in FIGS. 1–4.

Sanitary towels constructed in accordance with the present invention may, for instance, be produced in the manner illustrated schematically in FIG. 5. The absorbent blanks 1 are formed by air-laying cellulose fluff 7 in net-molds 9 disposed on a rotatable drum 8. The blanks 1 are thereafter placed on a moving conveyor belt 10, so as to lie between a liquid-impermeable web of material 11 and a liquid-permeable web of material 12, and is then passed between two rotating rollers 13, 14 which are set at a given mutual distance apart. The two webs 11, 12 are taken from two storage reels 15, 16, and at least one of the webs is coated with molten adhesive with the aid of a spray unit 17. The webs 11, 12 are bonded around the absorption blanks 1 in the compression stage, while the blanks 1 are bonded adhesively to the adhesive-coated web 11 at the same time.

The extent to which the absorption bodies are compressed, i.e. their degree of compression, is determined by a number of parameters, such as the spacing or nip between the rotating rollers, the moisture content of the fluff, and the type of fluff used. These factors influence each other and consequently it is not possible to define precisely the optimal setting of the compression rollers without having knowledge of the other parameters. For example, the moisture content of the fluff is of decisive significance to the compression result. Since the moisture content of a given fluff can vary with the time of the year, it is necessary to adapt the remaining parameters in accordance with this variation.

Subsequent to termination of the compression stage, the sanitary towels thus produced are mutually separated with the aid of cutting rollers and then transported to a packaging stage. The steps of separating and packaging the sanitary towels have not been shown in the drawing.

It will be understood that the described embodiments do not limit the invention and that a number of modifications are conceivable within the scope of the following claims.

For example, the compression rollers 13, 14 may be provided with promontories or protruding parts which function to exert additional high pressure on the centre part of the absorption bodies. This will ensure that the centre parts of said bodies are compressed to a sufficient extent to retain the compression during further handling of the sanitary towel up to the time of use.

I claim:

1. A method of producing an absorption body to be disposed in a casing of an absorbent article, said absorption body having longitudinally extending side edges, transversely extending end edges, the side edges being longer than the end edges, a center part and intermediate portions between the side edges and the center part, comprising the steps of:

forming out of absorbent material a blank having a generally triangular cross-sectional shape in a transverse direction;

compressing the blank over substantially an entire surface of the blank so as to form the absorption body having a density which continuously increases from the longitudinally extending side edges of the body transversely toward the center part of the body; and, performing the step of compressing by applying a compression force such that the intermediate portions of the blank will at least partially spring back when said compression force is relieved and such that the center part of said blank substantially retains the degree of compression achieved during said application of a compression force.

2. A method according to claim 1, wherein said compression force is applied by passing said blank between two compression rollers which are spaced from each other by a predetermined distance.

3. A method according to claim 2, wherein a greater compression force is applied to said center part of said blank than the compression force applied to other parts of said blank using protruding parts disposed on at least one of said two compression rollers.

4. A method according to claim 2, wherein a greater compression force is applied to said center part of said blank than the compression force applied to other parts of said blank.

5. A method according to claim 1, wherein a greater compression force is applied to said center part of said blank than the compression force applied to other parts of said blank.

6. A method according to claim 5, wherein said compression force is applied by passing said blank between two compression rollers which are spaced from each other by a predetermined distance and wherein said greater compression force is applied to said center part of said blank using protruding parts disposed on at least one of said two compression rollers.

7. A method according to claim 1, wherein said blank is formed by air-laying cellulose fluff into net-molds disposed in a rotatable suction drum.

8. An absorption body to be disposed in a casing of an absorbent article, comprising:

an absorbent fibrous material formed into a body having longitudinally extending side edges, transversely extending end edges, the side edges being longer than the end edges, a center part and intermediate portions between the side edges and the center part;

said absorbent material increasing in amount from said longitudinally extending side edges toward said intermediate portions and from said intermediate portions toward said center part;

said absorbent material increasing in density from said longitudinally extending side edges toward said center part;

said body being thinner at said center part than at said intermediate portions;

said body having a thickness that gradually increases from said center part toward said longitudinal side edges to a maximum and thereafter decreases.

9. An absorption body according to claim 8, wherein said center part forms a recess extending longitudinally along said absorbent material, said recess having a greater rigidity and a higher density than a rigidity and density in other areas of said absorbent material.

10. An absorption body according to claim 8, wherein said absorbent fibrous material is cellulose fluff.

11. An absorption body according to claim 8, wherein said absorbent material increases in density from said transversely extending end edges toward said center part.

12. An absorption body to be disposed in a casing of an absorbent article, comprising:

an absorbent fibrous material formed into a body having longitudinally extending side edges, transversely extending end edges, the side edges being longer than the end edges, a center part and intermediate portions between the side edges and the center part;

said absorbent material increasing in amount from said longitudinally extending side edges toward said intermediate portions and from said intermediate portions toward said center part;

said absorbent material increasing in density from said longitudinally extending side edges toward said intermediate portions and from said intermediate portions toward said center part;

said body being thinner at said center part than at said intermediate portions;

said body having a thickness that gradually increases from said center part toward said longitudinal side edges to a maximum and thereafter decreases.

13. An absorption body according to claim 12, wherein said center part forms a recess extending longitudinally along said absorbent material, said recess having a greater rigidity and a higher density than a rigidity and density in other areas of said absorbent material.

14. An absorption body according to claim 12, wherein said absorbent fibrous material is cellulose fluff.

15. An absorption body according to claim 12, wherein said absorbent material increases in density from said transversely extending end edges toward said center part.

* * * * *